May 10, 1955 F. M. STRINGHAM Re. 24,001

CATAMENIAL NAPKIN BELT

Original Filed March 31, 1952

Floyd M. Stringham

INVENTOR.

BY Clarence A. O'Brien and Harvey B. Jacobson

Attorneys

United States Patent Office

Re. 24,001

Reissued May 10, 1955

24,001

CATAMENIAL NAPKIN BELT

Floyd M. Stringham, Kennewick, Wash., assignor to Personal Products Corporation, North Brunswick Township, N. J., a corporation of New Jersey Original No. 2,633,847, dated April 7, 1953, Serial No. 279,588, March 31, 1952. Application for reissue December 15, 1954, Serial No. 475,596

5 Claims. (Cl. 128—291)

Matter enclosed in heavy brackets [ ] appears in the original patent but forms no part of this reissue specification; matter printed in italics indicates the additions made by reissue.

This invention relates to new and useful improvements and structural refinements in belts, particularly belts of the type which are commonly employed for suspending or sustaining in position catamenial napkins, and the principal object of the invention is to provide a belt of this character which may be conveniently and comfortably worn on the body in readiness for attachment of a napkin thereto as soon as an occasion to do so arises, and which will be effectively sustained in a proper position on the body regardless of any movement or change of posture to which the user may subject herself.

As is well known, conventional belts of this nature are not altogether comfortable or inconspicuous to wear, and as a result, the prospective user thereof customarily defers the installation of the belt on her body until the last moment, only to find that in many instances, the belt has been forgotten or misplaced and consequently is not available for immediate use.

Moreover, conventional belts, when subjected to downward pull by a napkin, slide down from the waistline both in front and at the back, so that the belt is only improperly supported at the sides by the hips, and eventually even these supporting regions become ineffective when the belt rolls down from the hips during normal movements of the body.

The instant invention eliminates these disadvantages by the provision of a belt which may be comfortably and inconspicuously worn per se, that is, without the napkin, to which the napkin may be quickly and easily attached when so desired, and which will dependably remain in position, without shifting, on the body.

Some of the advantages of the invention reside in its simplicity of construction and in its adaptability to economical manufacture.

With the above more important objects and features in view, and such other objects and features as may become apparent as this specification proceeds, the invention consists essentially of the arrangement and construction of parts as illustrated in the accompanying drawings, in which.

Like characters of reference are employed to designate like parts in the specification and throughout the several views.

Figure 1:
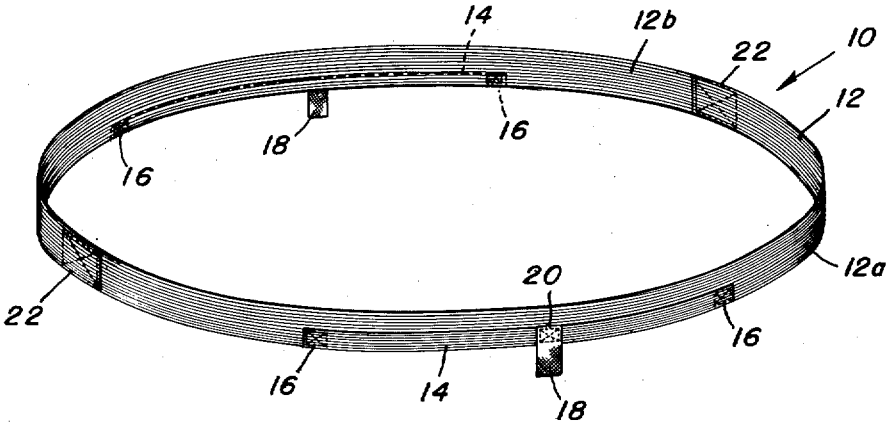
Figure 1 is a perspective view of the belt constructed in accordance with the invention.

Referring now to the accompanying drawings in detail, the invention consists of a catamenial napkin belt which is designated generally by the reference character 10 and embodies in its construction a waist encircling band 12 of resilient material, while a pair of resilient straps 14 are provided at the respective front and rear portions of the band, as is best shown in Figure 1. Each of these straps 14 is secured at both ends thereof to the band 12, such as for example, by stitching 16, and a pair of napkin attaching tabs 18 are secured by stitching 20 to the mid-portions of the respective straps 14, from which the tabs depend as shown.

The band 12 is substantially wider than the straps 14 and the two straps initially overlie the band and are secured thereto in such manner that the lower edges of the straps are in register with the lower edge of the band, as shown in Figure 1.

Figure 2:
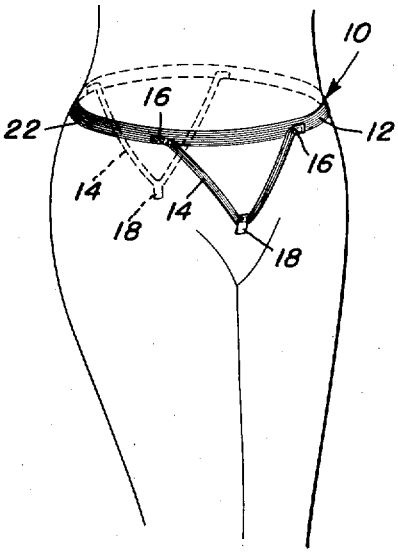
Figure 2 is a perspective view illustrating the belt in use.
Figure 3:
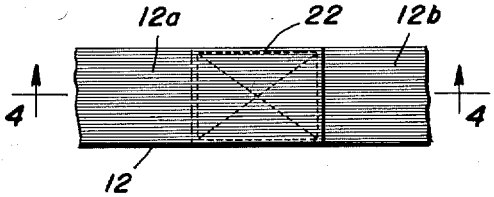
Figure 3 is a fragmentary elevational view showing the connection between the front and the rear sections of the belt; and, Figure 4 is a sectional detail, taken substantially on the plane of the line 4—4 of Figure 3.
Figure 4:
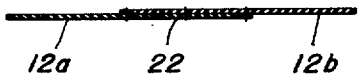

However, when the belt is to be placed in use in combination with the napkin, the straps 14 are pulled downwardly so that they assume a V-shaped position as shown in Figure 2, whereby a napkin (not shown) may be attached to the tabs 18 in any suitable manner. The V-shaped straps absorb the downward pull of the napkin by diverting it to opposite sides to the front and back, so that the belt is prevented from sliding, rolling or otherwise shifting from its proper position.

In order to prevent the band 12 from curling or twisting longitudinally when the straps are pulled downwardly, the band itself is preferably composed of two sections 12A, and 12B, which have overlapped end portions at the sides of the belt as secured together by stitching as indicated at 22.

It will be noted that when the belt is not in use for supporting a napkin, it may still be retained in position on the body, in which instance the straps 14 lie flatly on the band 12 so that the belt is not uncomfortable or inconspicuous to wear.

It is believed that the advantages and use of the invention will be readily understood from the foregoing disclosure and accordingly, further description thereof at this point is deemed unnecessary.

While in the foregoing there has been shown and described the preferred embodiment of this invention it is to be understood that minor changes in the details of construction, combination and arrangement of parts may be resorted to without departing from the spirit and scope of the invention as claimed.

Having described the invention, what is claimed as new is:

*1.* A catamenial napkin belt comprising a relatively wide resilient waist encircling band including complemental front and rear sections having overlapped end portions secured together at the sides of the band, a pair of relatively narrow resilient straps superposed longitudinally on the respective front and rear band sections and each permanently secured at both ends thereof to the associated band section, and a pair of napkin attaching tabs provided on mid-portions of the respective straps, said straps being normally straight and having their lower edges coplanar with lower edge portions of said band but being deformable into a substantially V-shaped configuration by a downward pull on said tabs.

*2. A catamenial napkin belt comprising a relatively wide resilient waist encircling band, a pair of relatively narrow resilient straps superposed longitudinally on the front and rear portions of said band and each permanently secured at both ends thereof to the band, said straps being normally straight and having their lower edges coplanar with the lower edge portions of said band but being deformable into a substantially V-shaped configuration by a downward pull on said straps.*

*3. A catamenial napkin belt comprising a relatively wide resilient waist encircling band, a pair of relatively narrow resilient straps superposed longitudinally on the front and rear portions of said band and each permanently secured at both ends thereof to the band, said band having means for imparting stiffness to the band at each*

*side thereof, said straps being normally straight and having their lower edges coplanar with the lower edge portions of said band but being deformable into a substantially* V-*shaped configuration by a downward pull on said straps.*

*4. A catamenial napkin belt comprising a relatively wide resilient waist encircling band, a pair of relatively narrow resilient straps superposed longitudinally on the front and rear portions of said band and each permanently secured at both ends thereof to the band, and napkin attaching means provided on the mid-portions of the respective straps, said straps being normally straight and having their lower edges coplanar with the lower edge portions of said band but being deformable into a substantially* V-*shaped configuration by a downward pull on said napkin attaching means.*

*5. A catamenial napkin belt comprising a relatively wide resilient waist encircling band, a pair of relatively narrow*

*resilient straps superposed longitudinally on the respective front and rear portions of said band and each permanently secured at both ends thereof to the band, and a pair of napkin attaching tabs provided on the mid-portions of the respective straps, said straps being normally straight and having their lower edges coplanar with the lower edge portions of said band but being deformable into a substantially* V-*shaped configuration by a downward pull on said tabs.*

References Cited in the file of this patent or the original patent

UNITED STATES PATENTS 1,801,161 Itkawitz et al. ---------- Apr. 14, 1931

FOREIGN PATENTS 261,198 Great Britain ---------- Nov. 18, 1926